United States Patent
Kato et al.

(10) Patent No.: US 10,799,841 B2
(45) Date of Patent: Oct. 13, 2020

(54) RECIPROCATING STIRRING APPARATUS HAVING MICRO BUBBLE GENERATING DEVICE

(71) Applicants: SATAKE CHEMICAL EQUIPMENT MFG LTD., Toda-shi, Saitama (JP); JGC CORPORATION, Tokyo (JP)

(72) Inventors: Yoshikazu Kato, Toda (JP); Hisayuki Kanamori, Toda (JP); Makoto Sato, Toda (JP); Naoki Tahara, Yokohama (JP); Hideaki Togashi, Yokohama (JP)

(73) Assignees: SATAKE CHEMICAL EQUIPMENT MFG LTD., Toda (JP); JGC JAPAN CORPORATION, Yokohama (JP)

( * ) Notice: Subject to any disclaimer, the term of this patent is extended or adjusted under 35 U.S.C. 154(b) by 138 days.

(21) Appl. No.: 15/322,650

(22) PCT Filed: Jun. 16, 2015

(86) PCT No.: PCT/JP2015/067224
§ 371 (c)(1),
(2) Date: Dec. 28, 2016

(87) PCT Pub. No.: WO2016/002492
PCT Pub. Date: Jan. 7, 2016

(65) Prior Publication Data
US 2017/0136429 A1    May 18, 2017

(30) Foreign Application Priority Data
Jul. 1, 2014 (JP) ................................. 2014-135678

(51) Int. Cl.
*B01F 13/10* (2006.01)
*B01F 11/00* (2006.01)
(Continued)

(52) U.S. Cl.
CPC ........ *B01F 13/1033* (2013.01); *B01F 3/0412* (2013.01); *B01F 3/04262* (2013.01);
(Continued)

(58) Field of Classification Search
CPC ................ B01F 11/008; B01F 11/0082; B01F 13/1033; B01F 11/0091; B01F 3/0412;
(Continued)

(56) References Cited

U.S. PATENT DOCUMENTS 4,923,817 A * 5/1990 Mundt ................ B01F 3/04531
435/286.6
6,844,186 B2 * 1/2005 Carll ................... B01F 11/0082
366/243

(Continued)

FOREIGN PATENT DOCUMENTS

CN        101987285 A       3/2011
DE        102006021984     * 11/2007
(Continued)

OTHER PUBLICATIONS

EPO translation of Werner et al. DE 10 2006 021 984 A1 published Nov. 15, 2007 (Year: 2007).*
(Continued)

*Primary Examiner* — Stephen Hobson
(74) *Attorney, Agent, or Firm* — Oliff PLC

(57) ABSTRACT

A reciprocating stirrer device with which favorable gas absorption into the stirred substance can be obtained. The reciprocating stirrer device is obtained from: a stirring vessel in which the substance to be stirred is placed; a reciprocating drive shaft provided inside the stirring vessel; a stirring blade connected and affixed so as to intersect the drive shaft; and a microbubble-generating unit. The microbubble-generating unit is obtained from a sparger that is made of a porous body and a gas supply means for supplying a gas to
(Continued)

the sparger. Bubbles are generated in the substance being stirred by passing gas supplied to the sparger by the gas supply means through pores of the porous body.

7 Claims, 6 Drawing Sheets

(51) Int. Cl.
  *B01F 3/04* (2006.01)
  *C12M 1/04* (2006.01)
  *B01F 15/00* (2006.01)
(52) U.S. Cl.
  CPC ...... *B01F 3/04269* (2013.01); *B01F 3/04531* (2013.01); *B01F 11/0082* (2013.01); *B01F 11/0091* (2013.01); *C12M 27/04* (2013.01); *B01F 11/008* (2013.01); *B01F 15/00467* (2013.01); *B01F 2003/0439* (2013.01); *B01F 2003/04205* (2013.01); *B01F 2003/04319* (2013.01); *B01F 2215/0073* (2013.01)
(58) Field of Classification Search
  CPC .............. B01F 3/04262; B01F 3/04269; B01F 3/04531; B01F 2003/04205; B01F 15/00467; B01F 2003/04319; B01F 2003/0439; B01F 2215/0073; C12M 27/04
  See application file for complete search history.

(56) References Cited

U.S. PATENT DOCUMENTS

| | | | | |
|---|---|---|---|---|
| 9,101,893 | B1* | 8/2015 | Pavlik | B01F 15/00155 |
| 9,289,764 | B2* | 3/2016 | Lange | B01F 1/0011 |
| 9,415,530 | B2* | 8/2016 | Fukuda | B29B 9/10 |
| 9,643,142 | B2* | 5/2017 | Pavlik | B01F 13/0238 |
| 2002/0011441 | A1* | 1/2002 | Drie | B01F 11/0082 |
| | | | | 210/513 |
| 2005/0127215 | A1* | 6/2005 | Lienhart | B01F 11/0082 |
| | | | | 241/21 |
| 2005/0249033 | A1* | 11/2005 | Krause | B01F 15/00831 |
| | | | | 366/332 |
| 2006/0196501 | A1* | 9/2006 | Bibbo | B01F 15/0085 |
| | | | | 128/200.23 |
| 2006/0270036 | A1* | 11/2006 | Goodwin | B01F 5/04 |
| | | | | 435/395 |
| 2009/0275121 | A1* | 11/2009 | Greller | B01F 15/0085 |
| | | | | 435/295.1 |
| 2010/0015696 | A1* | 1/2010 | Claes | C12M 23/26 |
| | | | | 435/303.3 |
| 2011/0026361 | A1* | 2/2011 | Sato | B01F 11/0082 |
| | | | | 366/343 |
| 2012/0244602 | A1* | 9/2012 | Okumura | B01F 3/0412 |
| | | | | 435/253.6 |
| 2013/0150618 | A1* | 6/2013 | Gobby | B01F 3/04531 |
| | | | | 560/232 |
| 2017/0333857 | A1* | 11/2017 | Barksdale | B01F 11/0082 |
| 2018/0012673 | A1* | 1/2018 | Omasa | G21G 7/00 |
| 2018/0195034 | A1* | 7/2018 | Brau | B01F 13/0272 |
| 2019/0345433 | A1* | 11/2019 | Prabhudharwadkar | |
| | | | | C12M 27/02 |

FOREIGN PATENT DOCUMENTS

| | | |
|---|---|---|
| JP | S61-167800 U | 10/1986 |
| JP | S64-23884 A | 1/1989 |
| JP | H02-286075 A | 11/1990 |
| JP | H05-292940 A | 11/1993 |
| JP | 2008-536685 A | 9/2008 |
| JP | 2011-031192 A | 2/2011 |
| KR | 10-2012-0104219 A | 9/2012 |
| WO | 2006/116067 A1 | 11/2006 |
| WO | 2011/070791 A1 | 6/2011 |

OTHER PUBLICATIONS

Aug. 25, 2015 International Search Report issued in International Patent Application No. PCT/JP2015/067224.
Jan. 29, 2018 Search Report issued in European Patent Application No. 15814240.6.
Aug. 14, 2018 Office Action issued in Korean Patent Application No. 10-2016-7036609.
Oct. 4, 2018 Office Action issued in Korean Patent Application No. 10-2016-7036609.
Jun. 25, 2018 Office Action issued in Japanese Patent Application No. 2016-531237.
Aug. 2, 2018 Office Action issued in Chinese Patent Application No. 201580033998.8.
Feb. 20, 2018 Office Action issued in Korean Patent Application No. 10-2016-7036609.
Aug. 25, 2015 Written Opinion of the International Searching Authority issued in Japanese Patent Application No. PCT/JP2015/067224.

* cited by examiner

RECIPROCATING STIRRING APPARATUS HAVING MICRO BUBBLE GENERATING DEVICE

TECHNICAL FIELD

The present invention relates to a reciprocating stirring apparatus having a micro bubble generating device.

BACKGROUND ART

Conventionally, as a method of favorably stirring a culture solution containing animal or plant cells or microorganisms without damaging the cells and the like, a vertically reciprocating stirring apparatus for stirring the culture solution by vertically reciprocating a stirring blade is known (Patent Literature 1).

The vertically reciprocating stirring apparatus can gently stir the culture solution by a low shearing action and favorably stir it and thus, it is suitable for stirring the culture solution containing cells and the like susceptible to damage.

CITATION LIST

Patent Literature

Patent Literature 1: Japanese Patent Laid-Open No. 2011-31192

SUMMARY OF INVENTION

Technical Problem

However, when gas such as oxygen, carbon dioxide or the like is supplied to the culture solution, bubbles having a diameter of approximately several nm, for example, bubbled from a sparger used in general cannot be made smaller (broken up) by the stirring blade due to stirring by the low shearing action in the conventional vertically reciprocating stirring apparatus, and there is a problem that a favorable gas absorbing action cannot be obtained.

The present invention relates to a reciprocating stirring apparatus which solves these problems and is capable of favorably stirring a culture solution (article to be stirred) and of rapidly dissolving gas such as oxygen or carbon dioxide or the like in the culture solution.

Solution to Problem

In order to achieve the aforementioned object, the present invention comprises a stirring container into which an article to be stirred is inserted, a driving shaft provided in the stirring container and performing a reciprocating motion, a stirring blade connected/fixed so as to cross the driving shaft, and a micro bubble generating device, the micro bubble generating device including a sparger constituted by a porous body having a cavity portion inside and gas supply means for supplying gas to the cavity portion in which the gas supplied by the gas supply means to the cavity portion is made to generate bubbles in the article to be stirred through pores of the porous body.

Advantageous Effects of Invention

According to the present invention, the culture solution (article to be stirred) is favorably stirred, and the gas such as oxygen or carbon dioxide or the like is rapidly dissolved into the culture solution.

Moreover, micro bubbles having a desired diameter can be generated.

Moreover, in the case of vertical stirring, the bubbles can be kept in contact with the article to be stirred for a long time.

Moreover, a favorable vertical flow can be realized regardless of presence of a sparger.

DESCRIPTION OF EMBODIMENT

An embodiment of the present invention will be described below.

Embodiment 1

An embodiment 1 of the present invention will be described by referring to FIGS. 1 to 7.

Figure 1:
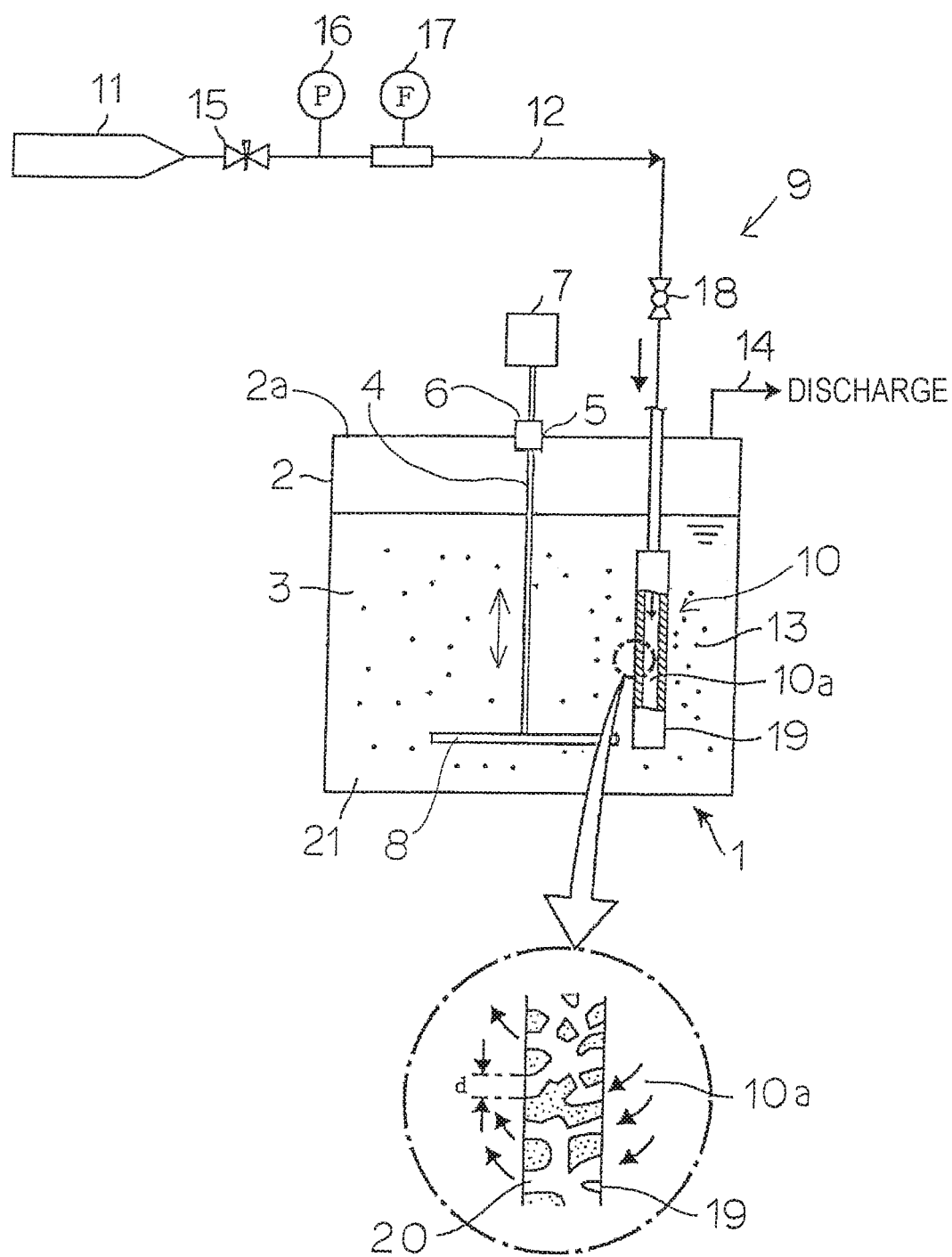
FIG. 1 is a vertical sectional view of a stirring apparatus of the present invention.

FIG. 1 is a vertical sectional view of a reciprocating stirring apparatus 1 of the present invention.

Reference numeral 2 denotes a stirring container of the reciprocating stirring apparatus 1 such as a culture vessel, for example, and the culture vessel 2 has a cylindrical body portion in which animal or plant cells or microorganisms and a culture solution (article to be stirred) 3 containing nutrients, for example, are contained.

Reference numeral 4 denotes a driving shaft, and the driving shaft 4 penetrates an opening portion 5 at a center part of a top surface portion 2a of the culture vessel 2 and is inserted into the culture vessel 2.

Moreover, the driving shaft 4 is supported capable of vertical motion by a driving-shaft seal portion provided on the opening portion 5 or a support portion 6 such as a thrust bearing and is connected to a reciprocating driving device 7 provided above the top surface portion 2a on an upper end portion of the driving shaft 4 so as to be vertically moved by driving of the reciprocating driving device 7.

Figure 2:
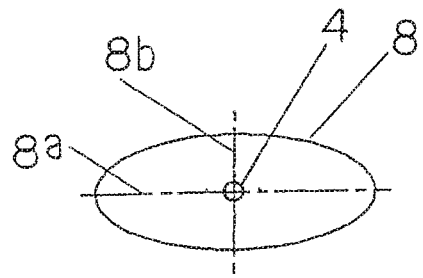
FIG. 2 is a plan view of a stirring blade of the stirring apparatus.

Reference numeral 8 denotes a stirring blade and as illustrated in FIG. 2, it is formed of an elliptic plate-shaped body and is connected/fixed to a lower end portion of the driving shaft 4 so as to cross it at a right angle.

In FIG. 2, reference character 8a denotes a long diameter of the ellipse of the stirring blade 8, while reference character 8b denotes a short diameter of the ellipse.

Figure 3:
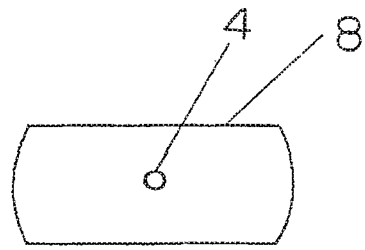
FIG. 3 is a plan view of the stirring blade of another embodiment of the stirring apparatus.

The stirring blade 8 is provided in one stage or two stages or more on the driving shaft 4, and a shape of the stirring blade 8 can be any shape such as an ellipse, an oval, a rectangle and the like, for example, as long as it has a long diameter and a short diameter and as illustrated in FIG. 3, edges on long diameter sides may be curved in a rectangle, for example. Moreover, only a corner portion of the stirring blade 8 may be curved. Moreover, a position where the stirring blade 8 is fixed to the driving shaft 4 may be on a middle stage or an upper stage, not on a lower end.

Reference numeral 9 denotes a micro bubble generating device, the micro bubble generating device 9 including a sparger 10, a gas storing portion 11, and a gas supply path 12, and the gas such as air, oxygen or the like is made by the sparger 10 to extremely fine bubbles (micro bubbles) 13 and is supplied to the culture solution 3 in the culture vessel 2.

Then, it is constituted such that the gas is supplied from the gas storing portion 11 in which the gas such as air, oxygen or the like is stored to the sparger 10 through the gas supply path 12, the fine bubbles 13 are supplied into the culture solution 3 from the sparger 10, and the gas (gas such as oxygen, carbon dioxide or the like) generated from inside the culture vessel 3 is discharged through a discharge path 14 connected to an upper surface of the culture vessel 2.

Reference numerals 15, 16, 17, and 18 in FIG. 1 denote a needle valve, a pressure gauge, a flowmeter, and a ball valve, respectively, and they are constituted such that supply/stop of the gas with respect to the culture vessel 2 and a pressure and a flow rate of the gas to be supplied to the culture vessel 2 are controlled by a controller, not shown, for example.

The sparger 10 described above is a tubular porous body extending in a vertical direction constituted by a porous body (porous membrane) 19 formed having a substantially cylindrical shape so that an inner region 10a thereof is hollow, for example, and is immersed in the culture solution 3.

A shape of the sparger 10 may be a shape other than the one linearly extending in the vertical direction. If it extends linearly in the vertical direction, a position where it is installed in the culture vessel may be located anywhere as will be described later, but by installing it on an outer side of the long diameter side of the stirring blade, the sparger 10 no longer influences a large circulation flow accompanied by a vertical flow and a swirling flow of the culture solution, which is preferable.

In this porous body 19, the air supply path 12 is hermetically connected to an upper end side, while a lower end side is sealed by a sealing member or the like, not shown, for example. In this porous body 19, as illustrated on a lower side in FIG. 1 in an enlarged manner, fine pores 20, each having a pore diameter d of 50 μm or less, for example, are formed in a large number uniformly over the entire surface so that an inner region 10a of the porous body 19 and an outer region (culture solution 3) of the sparger 10 communicate with each other through the pores 20 at a large number of positions.

This porous body 19 is obtained by, for example, mixing volcanic ash shirasu and glass raw material such as lime (CaO or $CaCO_3$) and boric acid ($H_3BO_3$), melting the resulting mixture at a high temperature, then, conducting a heat treatment at approximately 700° C., and then, conducting an acid treatment. That is, glass components in the porous body 19 are very uniformly separated into a first glass phase containing silica ($SiO_2$) and alumina ($Al_2O_3$) as main components and a second glass phase containing boron oxide ($B_2O_3$) and calcium oxide (CaO) as main components by the heat treatment and thus, after the acid treatment, the porous body 19 in which the very fine pores 20 are uniformly formed is obtained by adjusting the temperature and the time of the heat treatment, the amounts of the components added and the like. This porous body 19 is called, for example, shirasu porous glass (SPG) membrane and the like and is produced by SPG Technology Co., Ltd.

The culture solution 3 in the culture vessel 2 contains cells 21 or microorganisms, the cells 21 in this example, to be cultured and a nutrient serving as nutrition of the cells 21. This nutrient is a basal medium prepared by mixing plural types of amino acids, vitamins, inorganic salts, sugars and the like in a predetermined ratio, for example. Moreover, the culture solution 3 contains, as an additive, at least one of a protein hydrolysate and a cell-protecting agent for protecting the cells 21. Each of these additives has a surface-active action and suppresses coalescence (aggregation) of the fine bubbles 13 supplied from the sparger 10 described above into the culture solution 3 by the surface-active action. Specific components of these additives are described below in detail.

Other surface tension conditioners having the surface-active action may be also used.

The protein hydrolysate is a product obtained by hydrolyzing a protein to amino acids and low-molecular-weight peptides including a hydrolysate of casein, which is a protein derived from cow's milk, polypeptone, peptone, yeast extract, meat extract, and casamino acids, for example. Examples of the method of this hydrolysis include acidolysis, enzymolysis, and self-digestion. Peptone is a generic name of a compound obtained by hydrolyzing an animal protein or a vegetable protein to amino acids and low-molecular-weight peptides. Polypeptone, which is an example of peptone, is a product manufactured by Nihon Pharmaceutical Co., Ltd. and is a powder obtained by decomposing cow's milk casein with an enzyme derived from an animal, followed by purification and drying. Yeast extract is a powder obtained by extracting a water-soluble component of brewer's yeast (*Saccharomyces Cerevisiae* Meyen), followed by drying. An example of yeast extract is a product (product name: Dried yeast extract D-3) manufactured by Nihon Pharmaceutical Co., Ltd. Casamino acids are products obtained by hydrolyzing a protein to only amino acids using hydrochloric acid, the products being other than peptides. Note that this protein hydrolysate may be used instead of the nutrient described above.

Examples of the cell-protecting agent include Pluronic F68, Daigo's GF 21 (growth promoting factor), and serum. Pluronic F68 is a product (CAS No. 9003-11-6) manufactured by BASF Japan Ltd., and is a surfactant that does not have a function as a nutrient component or a cell growth promoting factor but that has a function of protecting the cells 21. Daigo's GF 21 is a product manufactured by Nihon Pharmaceutical Co., Ltd. and is a cell growth promoting factor containing, as a main component, a growth factor in serum (GFS) obtained by purifying bovine serum to remove γ-globulin. The serum is, for example, fetal calf serum or calf serum, and has not only a function of supplying a nutrient component and a cell growth factor but also a function of a cell-protecting agent that protects the cells 21 from physical stress due to stirring of the culture solution 3 and aeration during the culture of the cells.

Subsequently, an operation and an effect of the reciprocating stirring apparatus of this example will be described.

First, the cells 21, a nutrient, and at least one of the protein hydrolysate and the cell-protecting agent are charged in the culture vessel 2 together with the culture solution 3 described above. That is, in the case of serum culture, in addition to the cells 21, for example, the aforementioned basal medium and either serum or Daigo's GF21 are charged in the culture solution 3. In the case of serum-free culture, in addition to the cells 21, for example, the basal medium, a cell growth factor, and Pluronic F68 are charged. The amount of protein hydrolysate or cell-protecting agent added to the culture solution 3 is such that coalescence (aggregation) of the bubbles 13 can be suppressed by the surface-active action of the protein hydrolysate or the cell-protecting agent or specifically, the amount added is determined so that the surface tension of the culture solution 3 is 51.5 dyne/cm or less, for example. Note that, as described above, the protein hydrolysate may be used as the nutrient.

Then, gas containing oxygen or the like or air, for example, is supplied from the gas supply path 12 to the sparger 10 while the culture solution 3 in a culture tank 21 is controlled to a predetermined temperature by a heater, a jacket or the like, not shown.

Figure 4:
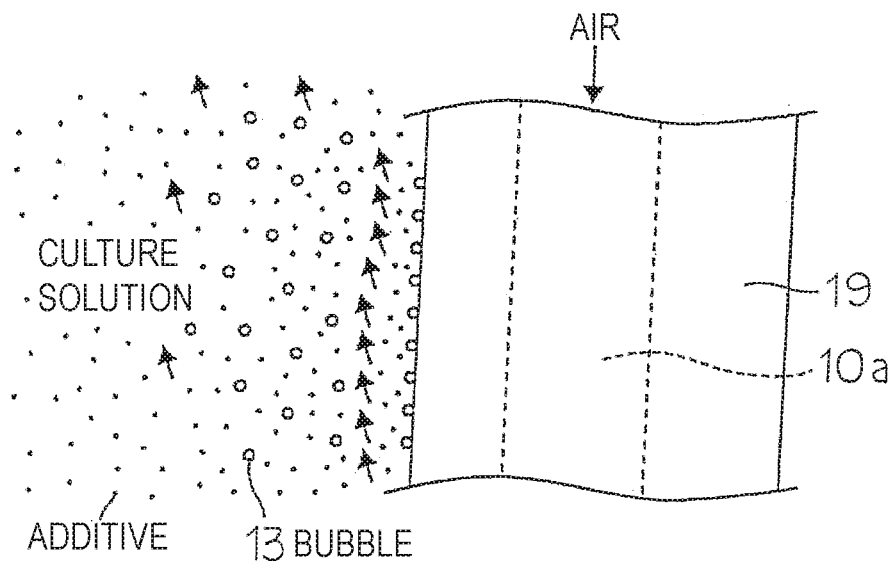
FIG. 4 is a schematic view illustrating a state in which bubbles are generated in the stirring apparatus.

As illustrated in FIG. 4, the air supplied from the sparger 10 into the culture solution 3 is pushed out as a large number of very small bubbles (micro bubbles) 13 each having a diameter of, for example, 200 μm or less from the pores 20 into the culture solution 3 through the inner region 10a of the porous body 19 and adheres to an outer surface of the porous body 19, for example. These bubbles 13 may coalesce (aggregate) with each other on the surface of the porous body 19 by, for example, the surface tension of the culture solution 3 but since the additive having a surface-active action is contained in the culture solution 3 as described above, the action of the surface tension is suppressed to be small, and thus, the coalescence is suppressed, and the bubbles are released into the culture solution 3 while maintaining the above fine size thereof.

Moreover, as described above, since the porous body 19 is composed of glass and has high wettability with the culture solution 3, the coalescence of the bubbles 13 on the surface of the porous body 19 is further suppressed. In FIG. 4, for the purpose of simplifying the illustration, the bubbles 13 are drawn only on one side of the porous body 19.

The coalescence of the bubbles 13 is also similarly suppressed in the culture solution 3 by the surface-active action of the additive. Accordingly, the particle diameter of the bubbles 13 (bubble diameters) in the culture solution 3 becomes very small and uniform, and thus, the bubbles 13 become micro bubbles having a 50% diameter (median size) of 200 μm or less in a volume-based particle size distribution. Consequently, the specific surface area of the bubbles 13 is increased to increase the contact area between air (bubbles 13) and the culture solution 3, as compared with the case where bubbles having a size of approximately several millimeters or 300 μm or more in the prior art are bubbled in the culture solution 3, for example. Note that the aforementioned volume-based particle size distribution is not a particle size distribution determined by counting the number of the bubbles 13 but a particle size distribution determined on the basis of the volume of the bubbles 13.

The aforementioned particle diameter (50% diameter) of the bubbles can be adjusted by a diameter of the pore and the surface tension as will be described later, and the bubbles with desired diameters can be generated by the diameter of the pore and the surface tension.

At this time, since the diameters of the bubbles 13 are very small, for example, 200 μm or less, the bubbles 13 are hardly affected by a buoyant force and are substantially in a so-called stationary state in the culture solution 3. Accordingly, the bubbles 13 move upward very slowly in the culture solution 3, and thus, the contact time with the culture solution 3 becomes longer than the case where the diameters of the bubbles are large.

Moreover, since the particle diameters of the bubbles 13 are extremely small as described above, an inner pressure (the force of the inner air to dissolve in the culture solution 3) of the bubbles 13 becomes larger than the bubbles each having a particle diameter of 300 μm or more, for example. Consequently, the bubbles 12 generated in the culture solution 3 are rapidly dissolved into the culture solution 13.

Moreover, in line with supply of the gas by the sparger 10 into the culture solution 3 in the culture vessel 2, the stirring blade 8 provided on the driving shaft 4 and the lower end portion thereof is reciprocated vertically by the reciprocating driving device 7 so as to conduct stirring (vertical vibration stirring) and to scatter the bubbles 13, supplied from the sparger 10 into the culture solution 3, into the culture solution 3.

The reciprocating motion (vibration) of the stirring blade 8 is not vibration by a high frequency such as ultra-vibration stirring but is vibration by a low shearing action based on a vertical motion of the stirring blade at 5 Hz or less, or preferably 2 Hz or less.

Figure 5:
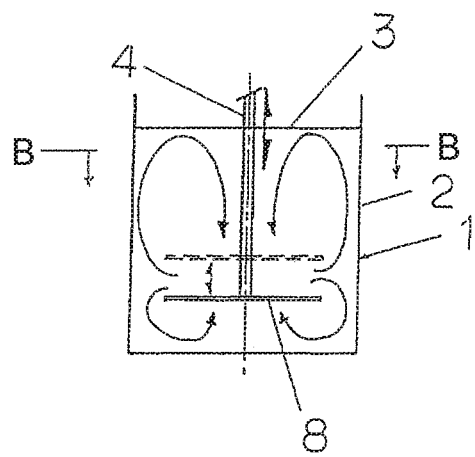
FIG. 5 is an explanatory view illustrating a flow pattern of vertical vibration stirring of the stirring apparatus.
Figure 6:
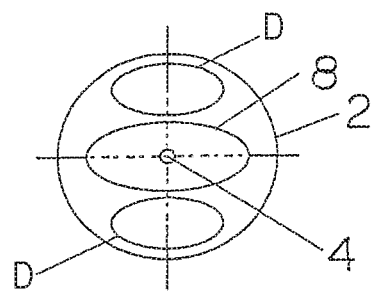
FIG. 6 is a B-B line cut-away view of FIG. 5.

Then, by means of the vertical stirring, a vertical flow reinforced region as indicated by D in FIG. 6 is formed on the outer side of the short diameter 8b portion of the stirring blade 8, and a large recirculation flow accompanied by a large vertical flow and a swirling flow accompanying it can be generated as illustrated in FIG. 5, whereby the bubbles 13 can be spread in the entire culture vessel 2.

Moreover, by making the stirring blade with an oval plate-shaped body, four corners of the stirring blade are made into arc shapes so as to prevent generation of a strong shearing action between a flow on the outer side of the long diameter and a flow on the outer side of the short diameter of the stirring blade in a stirring tank, and a large circulation flow accompanied by the large vertical flow and swirling flow can be generated on a side of the blade.

The cells 21 in the culture solution 3 consume oxygen in the culture solution 3 together with the nutrient and generate a product and carbon dioxide, for example. Then, as time elapses, the quantity (number of individuals) of the cells 21 in the culture solution 3 increases, and consumption of oxygen by the cells 21 increases as culturing of the cells 21 continuous. Accordingly, the oxygen dissolved in the culture solution 3 (dissolved oxygen) may decrease as time elapses.

However, by supplying the bubbles 13 from the sparger 10 into the culture solution 3 as described above and by spreading them in the entire culture vessel by the vertical vibration, the bubbles 13 are dissolved into the culture solution 3 as described above, and thus, the consumed portion of oxygen by the cells 21 is replenished.

That is, by supplying fine bubbles 13 into the culture solution 3 and stirring it, a decreasing speed of the dissolved oxygen concentration in the culture solution 3 becomes slower than the case of supply of bubbles with larger particle diameters or the decrease of the dissolved oxygen is suppressed. Carbon dioxide generated in the culture solution 3 is discharged from the discharge path 14. When consumption of the nutrient portion and oxygen by the cells 21 and an increase (culture) of the cells 21 progress for a certain period of time as above and the nutrient portion is exhausted, the cells 21 do not consume oxygen any more, and the dissolved oxygen concentration in the culture solution 3 rapidly increases.

Moreover, even in the case of the bubbles of 300 µm or more, for example, with a relatively large buoyant force, the rising bubbles are recirculated downward by the vertical flow, and thus, time of contact with the culture solution 3 can be taken long, and a favorable gas adsorbing force can be achieved.

According to the aforementioned embodiment, in culturing the cells 21 in the culture solution 3, air is supplied to the porous body 19 so as to generate very small bubbles 13 with the 50% diameter in the volume-based particle size distribution at 200 µm or less, and at least one of the protein hydrolysate and the cell-protecting agent is contained in the culture solution 3 as an additive. Therefore, by means of a surfactant action of this additive, coalescence (aggregation) of the bubbles 13 in the culture solution 3 is suppressed, and bubbles 13 with an extremely micro particle diameter can be obtained and thus, the contact area between gas and liquid (the bubbles 13 and the culture solution 3) can be taken more than the bubbles with the particle diameter of 300 µm or more, for example.

Moreover, since even the bubbles with a particle diameter of 300 µm or more, for example, with a relatively large buoyant force as the bubbles with 500 µm or less, the bubbles are recirculated downward by the vertical flow, the bubbles can be kept in contact with the culture solution for a long time, and a favorable gas adsorbing performance can be obtained.

Moreover, if the bubbles are 200 µm or less, a buoyant force of the bubbles 13 can be kept extremely low, and the bubbles 13 can be maintained in the culture solution 3 in a so-called stationary state as compared with the bubbles with the large particle diameter described above. Accordingly, the bubbles 13 can be kept in contact with the culture solution 3 for a long time, oxygen can be rapidly dissolved in the culture solution 3. Moreover, in the fine bubbles 13, since the pressure of the air inside to be dissolved out to the outer side of the bubbles becomes larger than the bubbles with a larger particle diameter, oxygen can be dissolved in the culture solution 13 more rapidly.

Furthermore, it is not necessary to conduct stirring vigorously to such an extent that the large bubbles are broken up in order to obtain the bubbles 13 described above, and the entire inside of the culture vessel can be stirred by the vertical stirring by the low shearing action without damaging the cells and favorable stirring can be achieved by the low shearing action.

Moreover, since it is not necessary to break up the bubbles 13, damage to the cells 2 caused by an impact when the bubbles 12 are broken up can be suppressed. Moreover, when the additive is added to the culture solution 3, since the culture solution 3 is a liquid used for culturing the cells 21, substances other than the protein hydrolysate and the cell-protecting agent, for example, substances harmful to the cells 21 or to the culture solution 3 to culturing of the cells 21 cannot be added to the culture solution 3, but in the present invention, additives beneficial to the culture of the cells 21 can be used. Thus, oxygen can be rapidly supplied to the culture solution 13 without adversely affecting the culture of the cells 21.

Figure 7:
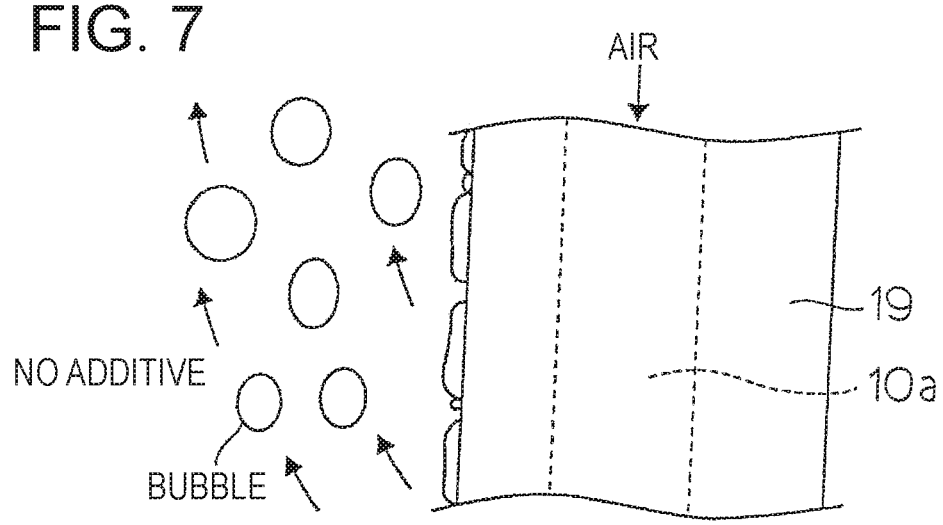
FIG. 7 is a schematic view illustrating a state in which the sir bubbles are generated by a prior-art method.

In the case where the above additive is not contained in the culture solution 3, even when fine bubbles 13 are generated by using the sparger 10, as illustrated in FIG. 7, the bubbles 13 are immediately coalesced, for example, on the surface of the porous body 19 by the surface tension of the culture solution 3, resulting in the generation of large bubbles. In FIG. 7, similarly, the bubbles are drawn only on one side of the porous body 11.

However, even in the case where the additive is not contained and large bubbles are generated, if the diameter of the generated bubbles is 1 mm or less or preferably 500 µm or less, for example, the bubbles can be kept in contact with the culture solution for a long time by the vertical flow, and the favorable gas absorbing action can be exerted.

Moreover, since the vertical flow and the swirling flow accompanying it are generated by the vertical stirring of the present application, even if the sparger 10 extending in the vertical direction is installed at an arbitrary position in the culture vessel, the sparger 10 does not obstruct the large recirculation flow.

By installing the tubular sparger 10 extending in the vertical direction on the outer side on the long diameter side of the stirring blade 8, favorable stirring can be realized without fully obstructing the large recirculation flow.

Moreover, by providing the sparger 10 extending vertically at a center of the large recirculation flow where the vertical flow and the swirling flow are generated, the favorable stirring can be realized without obstructing the large circulation flow.

If stirring by a rotary blade is employed instead of vertical stirring, rotation needs to be gentle in order to eliminate the low shearing action, but if the rotation is made gentle as above, there is a concern that stirring of the culture solution becomes insufficient, but according to the vertical stirring of the invention of the present application, the low shearing action can be maintained regardless of the frequency of vibration in the vertical direction, the culture solution can be sufficiently stirred, and favorable stirring can be realized.

Moreover, if stirring by the rotary blade is employed instead of the vertical stirring, a rotating flow is generated in the culture vessel, but the sparger 10 extending in the vertical direction obstructs the rotating flow, favorable stirring cannot be conducted and a low shearing action cannot be realized, but such a thing does not occur in the invention of the present application.

In the above example, the cells 21 are cultured by supplying gas containing oxygen such as air, but the present invention may be applied when a plant such as plant cells or microalgae is cultured by supplying gas containing carbon dioxide. In this case, too, since fine bubbles 13 of the gas containing carbon dioxide are generated in the culture solution 3 through the sparger 10, carbon dioxide can be rapidly dissolved in the culture solution 3 as in the example described above. In such a case, a protein hydrolysate and a cell-protecting agent are used as additives added in order to reduce the particle diameter of the bubbles 13 (in order to reduce the surface tension of the culture solution 3). The amounts of additives added are appropriately set on the basis of, for example, experiments.

In this embodiment, the example in which the driving shaft 4 is suspended and the driving shaft 4 is moved in the vertical direction is illustrated, but the driving shaft 4 may be directed to an arbitrary direction and reciprocated in the arbitrary direction such that the driving shaft 4 is laterally provided and moved laterally.

EXAMPLES

Subsequently, experiments conducted regarding micro bubbles 13 will be described.

Example 1

First, in the case where a cell-protecting agent (Daigo's GF21) was added to the culture solution 3 for culturing animal cells, a particle size distribution of bubbles 13 generated from the aforementioned sparger 10 (porous body 19 having a pore diameter of 1 μm) was measured. The particle diameter was measured using a laser diffraction/scattering particle size distribution analyzer by continuously supplying the culture solution 3, in which the bubbles 13 were generated by the sparger 10, to a flow cell in the particle size distribution analyzer, irradiating the culture solution 3 with a laser beam, and by evaluating diffraction or scattering of the laser beam.

Figure 8:
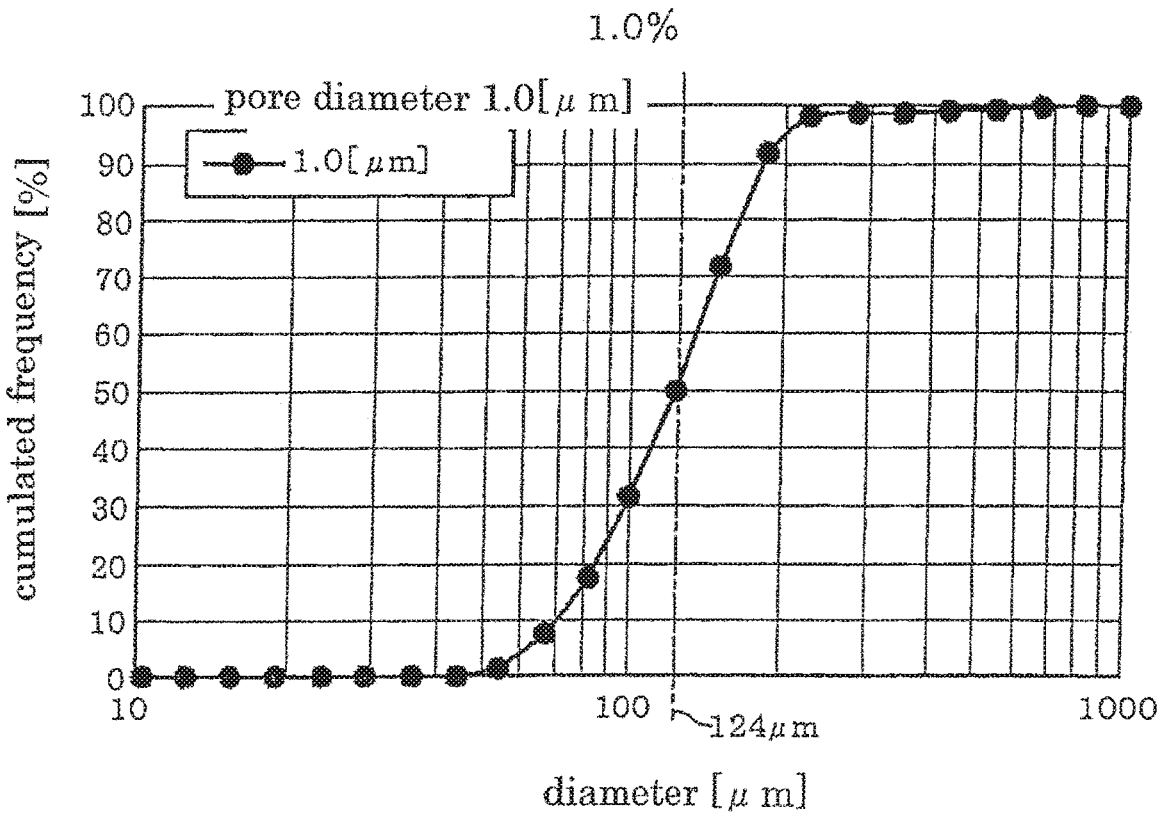
FIG. 8 is a characteristic illustrating a result obtained by an example of the present invention.
Figure 9:
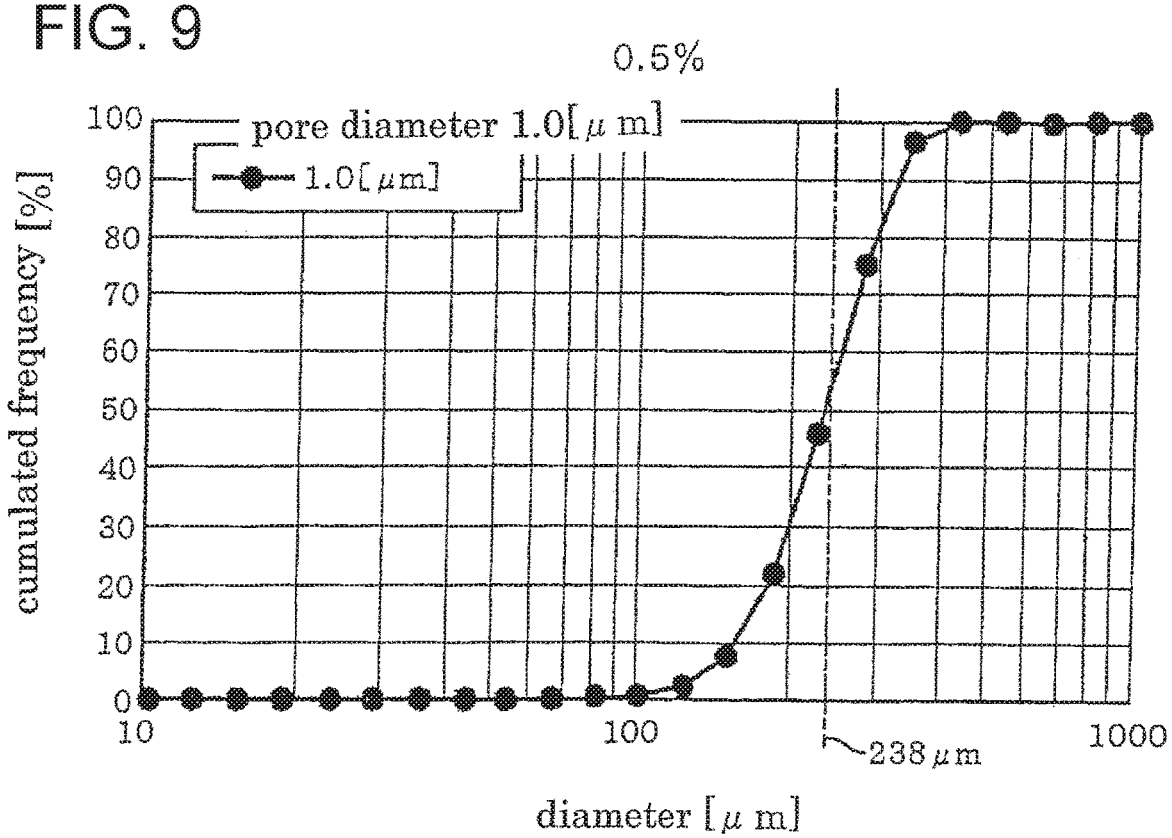
FIG. 9 is a characteristic illustrating a result obtained by the example of the present invention.
Figure 10:
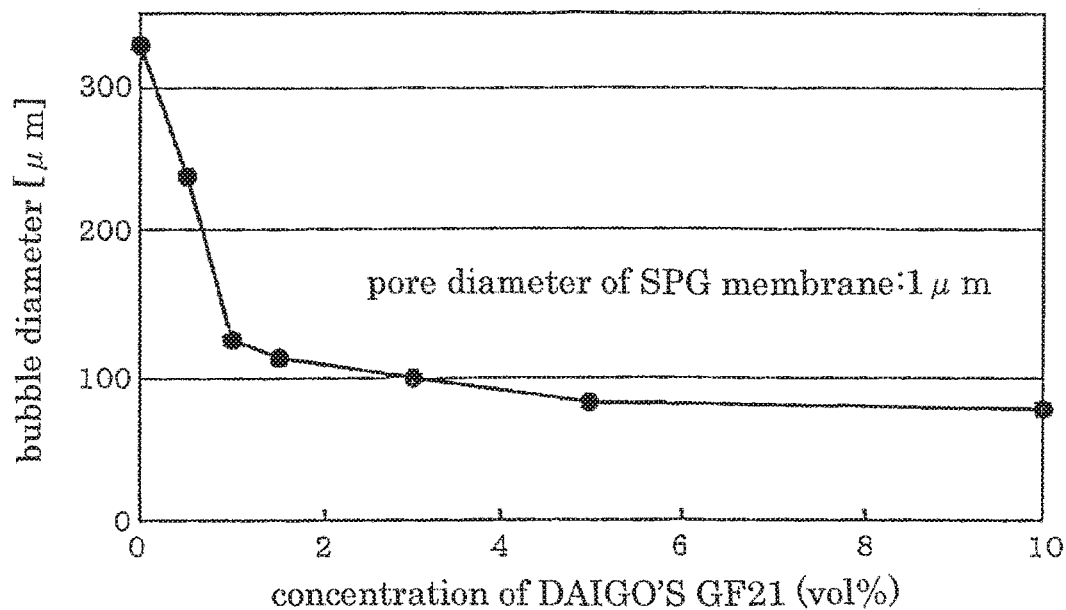
FIG. 10 is a characteristic illustrating a result obtained by the example of the present invention.

As a result, in the case where the amount of cell-protecting agent added was 1% by volume, as illustrated in FIG. 8, a 50% diameter in a volume-based particle size distribution was 200 μm or less (124 μm). Accordingly, it is believed that the influence of the buoyant force is very small in the bubbles 13 having this size as described above. On the other hand, in the case where the amount of cell-protecting agent added was 0.5%, as illustrated in FIG. 9, the 50% diameter was 238 μm. To examine the relationship between the amount of additive added and the particle diameter of the bubbles 13 obtained, the particle diameter of the bubbles 13 was measured for various amounts of Daigo's GF21 added, and the results illustrated in FIG. 10 were obtained. Accordingly, it was found that, in order to generate bubbles 13 having a particle diameter of 200 μm or less, the bubbles being believed to be less affected by the buoyant force, it is necessary to add 1% by volume or more of Daigo's GF21.

Example 2

To examine the correlation between the amount of additive added and the particle diameter of bubbles 13 generated, experiments were conducted as in Example 1 for various types and amounts of additive added.

Figure 11:
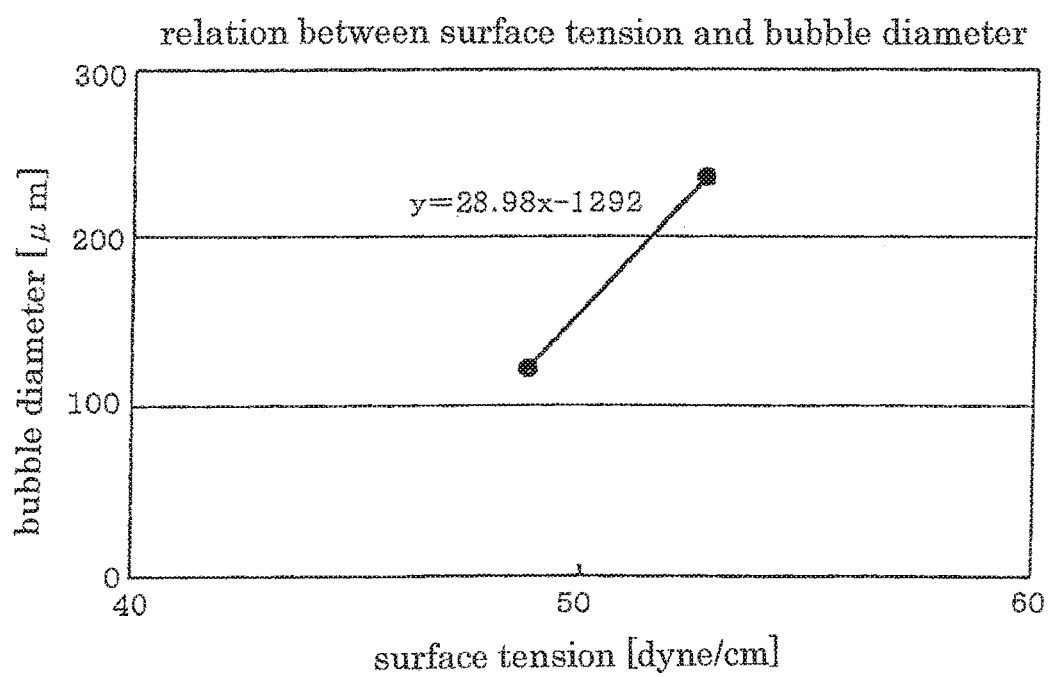
FIG. 11 is a characteristic illustrating a result obtained by the example of the present invention.

First, as described above, since the particle diameter of the bubbles 13 generated varies depending on the surface tension of the culture solution 3, the surface tension of the culture solution 3 required for generating fine bubbles 13 having a particle diameter of 200 μm or less was examined. Specifically, the bubbles 13 were generated using the sparger 10 described above in the culture solutions 3 containing various amounts of Daigo's GF21 as an additive, and the surface tension of each of the culture solutions 3 and the particle diameter of the bubbles 13 generated were measured. As a result, as illustrated in FIG. 11, there was a linear correlation between the surface tension of the culture solution 3 and the particle diameter of the bubbles 13 generated, and it was found that the relationship is represented by a formula (1) below:

$$y = 28.98x - 1292 \tag{1}$$

From this formula (1), it was found that, in order to generate the bubbles 13 having a fine particle diameter of 200 μm or less as described above, it is necessary to control the surface tension of the culture solution 3 to be 51.5 dyne/cm or less.

Regarding the additives listed in Tables 1 to 3 below, the surface tension of the culture solutions 3 was evaluated for various concentrations of each of the additives. In the case where such fine bubbles 13 were believed to be generated (the surface tension was 51.5 dyne/cm or less), the result was denoted by "○", and in the case where bubbles 13 having a particle diameter larger than the above were believed to be generated (the surface tension was more than 51.5 dyne/cm), the result was denoted by "×". Tables 1 to 3 below show the results:

TABLE 1

| | | Concentration [mg/L] | | | | | | | | |
|---|---|---|---|---|---|---|---|---|---|---|
| | | 濃度 (mg/L) | | | | | | | | |
| Component | 成分 | 1 | 5 | 10 | 50 | 100 | 500 | 1000 | 5000 | 10000 |
| Polypeptone | ポリペプトン | x | x | x | x | x | x | x | x | ○ |
| Yeast extract | 酵母エキス | x | x | x | x | x | x | x | ○ | ○ |

TABLE 2

| | | Concentration [mg/L] | | | | | | | | |
|---|---|---|---|---|---|---|---|---|---|---|
| | | 濃度 (mg/L) | | | | | | | | |
| Component | 成分 | 0 | 0.1 | 0.25 | 0.5 | 1 | 10 | 100 | 1000 | 10000 |
| Pluronic F68 | プルロニック F68 | x | x | x | x | x | ○ | ○ | ○ | ○ |

TABLE 3

| | | Concentration [vol %] | | | | | | | |
|---|---|---|---|---|---|---|---|---|---|
| | | 濃度 [vol %] | | | | | | | |
| Component | 成分 | 0 | 0.2 | 0.5 | 1 | 1.5 | 2 | 3 | 5 | 10 |
| Daigo's GF21 | ダイゴ GF21 | x | x | x | ○ | ○ | ○ | ○ | ○ | ○ |

From these results, it was found that, in order to obtain bubbles 13 having a particle diameter 200 μm or less, for example, the bubbles 13 being believed to be less affected by the buoyant force, it is necessary to adjust the amount of additive added in accordance with the type of additive.

Example 3

Figure 12:
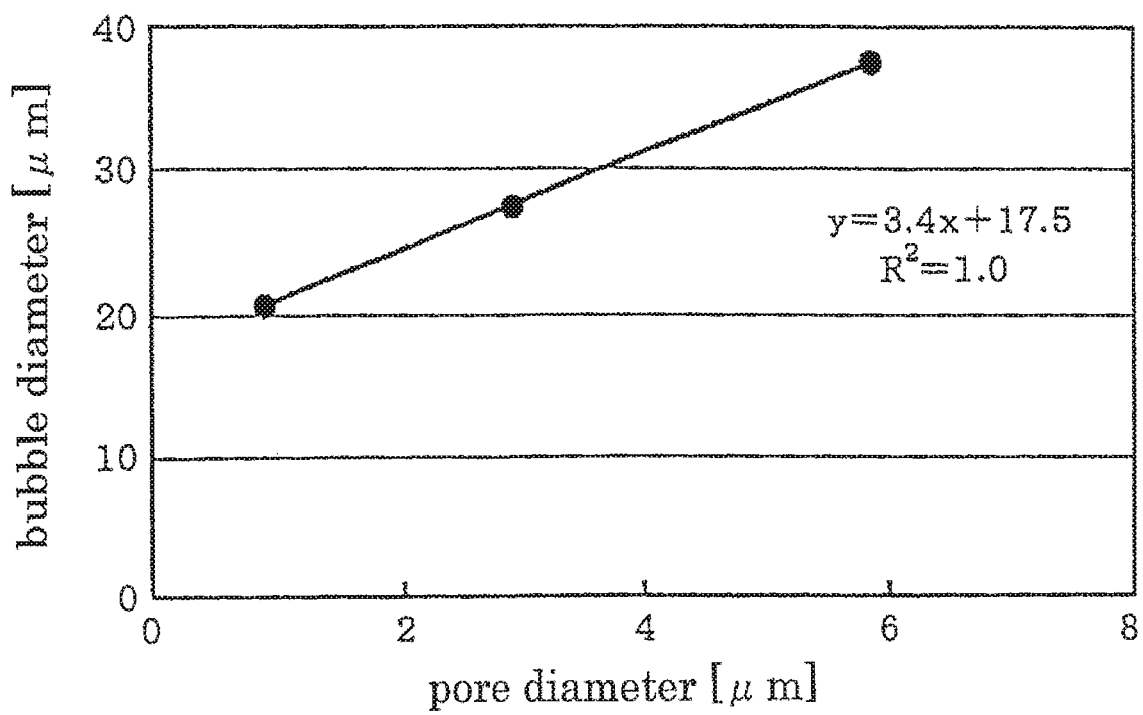
FIG. 12 is a characteristic illustrating a result obtained by the example of the present invention.

Subsequently, in a culture medium (surface tension: 48.6 dyne/cm) for culturing microorganisms, the relationship between the bubble diameter of the bubbles 13 and a pore diameter d of the porous body 19 was measured, and the results illustrated in FIG. 12 were obtained. A linear expression that approximates the above relationship was calculated as follows on the basis of the results:

$$y = 3.4x + 17.5 \tag{2}$$

(x: the pore diameter of the porous body 19, y: particle diameter (50% diameter) of the bubbles 13). The $R^2$ value in this case is 1.0 and thus, it is found that the pore diameter d of the porous body 19 can be calculated with high accuracy by the formula (2) from the particle diameter of the bubbles 13 in the culture solution 3. Accordingly, the pore diameter d of the porous body 19 corresponding to the particle diameter (200 μm) of the bubbles 13, which are believed to be hardly affected by the buoyant force, was calculated, and the pore diameter d was found to be 50 μm. Thus, fine bubbles 13 which are hardly affected by the buoyant force can be obtained by using the porous body 19 having the pore diameter d of 50 μm or less.

INDUSTRIAL APPLICABILITY

The reciprocating stirring apparatus of the present invention is used in fields relating to medical products, food products and the like.

REFERENCE SIGNS LIST 1 reciprocating stirring apparatus
2 culture vessel
2a top surface portion
3 culture solution
4 driving shaft
5 opening portion
6 support portion
7 reciprocating driving device
8 stirring blade
8a long diameter
8b short diameter
9 micro bubble generating device
10 sparger
10a inner region
11 gas storing portion
12 gas supply path
13 bubble
14 discharge path
16 needle valve
16 pressure gauge
17 flow meter
18 ball valve
19 porous body
20 pore
21 cell

The invention claimed is:

1. A reciprocating stirring apparatus, comprising:
a stirring container into which an article to be stirred is inserted;
a driving shaft provided in the stirring container and performing a reciprocating motion;
a stirring blade connected/fixed so as to cross the driving shaft and to receive the reciprocating motion therefrom, wherein the stirring blade has a rectangular, an elliptic or an oval shape made of a long diameter and a short diameter, and
a micro bubble generating device, wherein
the micro bubble generating device includes a sparger formed of a porous body and a gas supply for supplying gas to the sparger,
the gas supplied by the gas supply to the sparger is made to generate bubbles in the article to be stirred through pores of the porous body, and
the sparger is tubular extending in an axial direction of the driving shaft and is provided on an outside of the long diameter of the stirring blade.

2. The reciprocating stirring apparatus according to claim 1, wherein the porous body is formed of shirasu porous glass.

3. The reciprocating stirring apparatus according to claim 2, further comprising a surface tension conditioner to be added to the article to be stirred.

4. The reciprocating stirring apparatus according to claim 3, wherein by adjusting a diameter of a pore of the porous body and an amount of the surface tension conditioner, the bubbles having a desired diameter are generated from the micro bubble generating device.

5. The reciprocating stirring apparatus according to claim 1, further comprising a surface tension conditioner to be added to the article to be stirred.

6. The reciprocating stirring apparatus according to claim 5, wherein
by adjusting a diameter of a pore of the porous body and an amount of the surface tension conditioner, the bubbles having a desired diameter are generated from the micro bubble generating device.

7. The reciprocating stirring apparatus according to claim 1, wherein the reciprocating motion of the stirring blade is 5 Hz or less.

* * * * *